(12) United States Patent
Miyamoto et al.

(10) Patent No.: US 10,195,131 B2
(45) Date of Patent: Feb. 5, 2019

(54) ORAL COMPOSITION FOR ALLEVIATION OF DENTIN HYPERSENSITIVITY

(71) Applicant: NOF CORPORATION, Tokyo (JP)

(72) Inventors: Koji Miyamoto, Kawasaki (JP); Nobuyuki Yamamoto, Kawasaki (JP); Shunsuke Sakurai, Kawasaki (JP); Yoshihisa Shimamura, Kawasaki (JP)

(73) Assignee: NOF CORPORATION, Shibuya-ku, Tokyo (JP)

( * ) Notice: Subject to any disclaimer, the term of this patent is extended or adjusted under 35 U.S.C. 154(b) by 0 days.

(21) Appl. No.: 15/507,115

(22) PCT Filed: Jul. 27, 2015

(86) PCT No.: PCT/JP2015/071197
§ 371 (c)(1),
(2) Date: Feb. 27, 2017

(87) PCT Pub. No.: WO2016/031461
PCT Pub. Date: Mar. 3, 2016

(65) Prior Publication Data
US 2017/0281502 A1    Oct. 5, 2017

(30) Foreign Application Priority Data
Aug. 29, 2014  (JP) .................................. 2014-174782

(51) Int. Cl.
| | | |
|---|---|---|
| A61Q 11/00 | (2006.01) | |
| A61K 8/55 | (2006.01) | |
| A61K 8/34 | (2006.01) | |
| A61K 8/24 | (2006.01) | |
| C08F 230/02 | (2006.01) | |
| A61K 8/81 | (2006.01) | |

(52) U.S. Cl.
CPC .................. *A61K 8/55* (2013.01); *A61K 8/24* (2013.01); *A61K 8/34* (2013.01); *A61K 8/345* (2013.01); *A61K 8/8152* (2013.01); *A61Q 11/00* (2013.01); *C08F 230/02* (2013.01)

(58) Field of Classification Search
None
See application file for complete search history.

(56) References Cited

U.S. PATENT DOCUMENTS

| | | |
|---|---|---|
| 6,048,913 A | 4/2000 | Yamagishi et al. |
| 6,241,972 B1 | 6/2001 | Herms et al. |
| 2002/0041852 A1 | 4/2002 | Napolitano et al. |
| 2003/0215401 A1 | 11/2003 | Estrada et al. |
| 2007/0059257 A1 | 3/2007 | Estrada et al. |
| 2013/0263395 A1 | 10/2013 | Boyd et al. |

FOREIGN PATENT DOCUMENTS

| | | | |
|---|---|---|---|
| JP | 07-506138 A | 7/1995 | |
| JP | 2004-506663 A | 3/2004 | |
| JP | 2005-068071 A | 3/2005 | |
| JP | 2006-273767 | * 10/2006 | ............. A61Q 11/00 |
| JP | 2006-273767 A | 10/2006 | |
| JP | 3889449 B2 | 3/2007 | |
| JP | 2007-217516 A | 8/2007 | |
| JP | 2011-153101 | * 8/2011 | ............... A61K 8/81 |
| JP | 2011-153101 A | 8/2011 | |
| JP | 2013-545801 A | 12/2013 | |
| WO | 93/21970 A | 11/1993 | |
| WO | 00/48561 A1 | 8/2000 | |
| WO | 2011/055709 A1 | 5/2011 | |

OTHER PUBLICATIONS

International Preliminary Report on Patentability with a Translation of Written Opinion issued from the International Bureau in counterpart International Application No. PCT/JP2015/071197, dated Mar. 9, 2017.
European Patent Office, Communication dated Jan. 19, 2018, issued in counterpart European Application No. 15835822.6.
International Searching Authority, International Search Report for PCT/JP2015/071197 dated Oct. 20, 2015.

* cited by examiner

*Primary Examiner* — Brian Gulledge
(74) *Attorney, Agent, or Firm* — Sughrue Mion, PLLC (57) ABSTRACT

An oral composition for reducing dentinal hypersensitivity according to the present invention comprises a phosphorylcholine-containing polymer as an active ingredient. A general consumer can use the oral composition routinely in various forms. The oral composition is brought into contact with an oral cavity of a user to reduce the dentinal hypersensitivity.

14 Claims, 2 Drawing Sheets

ORAL COMPOSITION FOR ALLEVIATION OF DENTIN HYPERSENSITIVITY

CROSS REFERENCE TO RELATED APPLICATIONS

This application is a National Stage of International Application No. PCT/JP2015/071197 filed Jul. 27, 2015, claiming priority based on Japanese Patent Application No. 2014- 174782 filed Aug. 29, 2014, the contents of all of which are incorporated herein by reference in their entirety.

FIELD OF ART

The present invention relates to an oral composition containing a phosphorylcholine-containing polymer as an active ingredient, usable as a dentinal hypersensitivity-reducing agent.

BACKGROUND ART

A painful symptom of dentinal hypersensitivity is caused by a tissue fluid flow change in a dentinal tubule due to a physical stimulus of teeth grinding, brushing, or the like, a stimulus with cold water, etc. It is considered that this symptom is caused when an enamel for blocking the external stimulus is peeled off or a gum is lowered due to a periodontal disease or advancing age, whereby a dentin is exposed and the stimulus is transmitted directly to a dental pulp through the dentinal tubule.

Therefore, in several known methods, the dentinal tubule is physically protected to prevent the transmission of the stimulus to the dental pulp. For example, a method containing forming a polymer membrane on the exposed dentin surface to reduce the dentinal hypersensitivity, a method containing forming a hard coating of an adhesive resin, and the like have been known. However, only qualified dentists can perform these methods. General consumers cannot utilize the methods routinely.

In a known method that general consumers can utilize routinely, an oral composition containing aluminum lactate for protecting the dentinal tubule or potassium nitrate for reducing a sensitivity of a dental pulp cell is used to reduce the dentinal hypersensitivity.

However, the aluminum lactate and potassium nitrate each have an inherent bitter, astringent, or harsh taste. Patent Literature 1 discloses a method for reducing the unpleasant taste.

In addition, the potassium nitrate is disadvantageously less soluble in the case of using the potassium nitrate in combination with sodium lauryl sulfate. Patent Literature 2 discloses a technology for preventing precipitation of the potassium nitrate at low temperature.

Furthermore, Patent Literature 3 discloses a phosphorylcholine-containing polymer usable in an oral composition, and Patent Literature 4 discloses a method using the phosphorylcholine-containing polymer in the oral composition to prevent microbial adhesion in an oral cavity.

Patent Literature 5 discloses usefulness of the phosphorylcholine-containing polymer in dentistry. Specifically, Patent Literature 5 describes a technology for preventing adhesion of a microorganism such as a mold or fungus to a tooth surface.

Patent Literature 6 discloses that the phosphorylcholine-containing polymer can be used in a hypersensitivity-reducing agent in the dental material field. Specifically, Patent Literature 6 discloses a dental composition containing the phosphorylcholine-containing polymer as a tooth surface coating agent.

CITATION LIST

Patent Literature 1: WO 2011/055709
Patent Literature 2: JP 2005-68071 A
Patent Literature 3: JP 2006-273767 A
Patent Literature 4: JP 2011-153101 A
Patent Literature 5: JP 07-506138 T
Patent Literature 6: JP 2007-217516 A

SUMMARY OF THE INVENTION

Problems to be Solved by the Invention

The dentinal hypersensitivity-reducing methods disclosed in Patent Literatures 1 and 2 using the composition containing the potassium nitrate are disadvantageous in that the contents of the ingredients are limited as described above. The technology disclosed in Patent Literature 6 for coating a tooth surface with the phosphorylcholine-containing polymer to reduce the hypersensitivity should be performed by a dentist or the like.

An object of the present invention is to provide an oral composition that a general consumer can use routinely as a dentinal hypersensitivity-reducing agent.

Another object of the present invention is to provide use of a phosphorylcholine-containing polymer that a general consumer can perform routinely for reducing dentinal hypersensitivity.

A further object of the present invention is to provide a method that a general consumer can perform routinely for reducing dentinal hypersensitivity.

Means for Solving the Problem

As a result of intense research in view of the above objects, the inventors have found that a general consumer per se can easily reduce dentinal hypersensitivity using a preparation containing a phosphorylcholine-containing polymer as an active ingredient. The present invention has been accomplished based on this finding.

According to an aspect of the present invention, there is provided an oral composition for reducing dentinal hypersensitivity comprising a phosphorylcholine-containing polymer as an active ingredient.

It is preferred that the phosphorylcholine-containing polymer comprises at least one polymer selected from the group consisting of homopolymers of 2-methacryloyloxyethyl phosphorylcholine (hereinafter may be referred to as MPC), copolymers of MPC and butyl methacrylate, copolymers of MPC and stearyl methacrylate, and copolymers of MPC and 2-hydroxy-3-methacryloyloxypropyl trimethyl ammonium chloride.

In the present invention, the weight-average molecular weight (Mw) of the phosphorylcholine-containing polymer is preferably 10,000 to 10,000,000, more preferably 50,000 to 5,000,000.

The oral composition of the present invention preferably contains 0.001% to 10% by mass of the phosphorylcholine-containing polymer.

The oral composition of the present invention preferably has a pH of 5 to 11.

It is preferred that the oral composition of the present invention further contains at least one ingredient selected from the group consisting of glycerin, sorbitol, maltitol, and xylitol. It is further preferred that the oral composition contains 1% to 25% by mass of the ingredient.

According to another aspect of the present invention, there is provided use of the phosphorylcholine-containing polymer for reducing dentinal hypersensitivity.

According to a further aspect of the present invention, there is provided a method for reducing dentinal hypersensitivity comprising bringing the oral composition into contact with an oral cavity of a user.

Effect of the Invention

The oral composition of the present invention for reducing dentinal hypersensitivity contains the phosphorylcholine-containing polymer as an active ingredient. A general consumer can use the oral composition in daily life, and can reduce the dentinal hypersensitivity easily and effectively.

Particularly in a case where the oral composition contains at least one ingredient selected from the group consisting of glycerin, sorbitol, maltitol, and xylitol, the oral composition can exhibit an enhanced moisturizing effect in an oral cavity in addition to the effect of reducing the dentinal hypersensitivity.

EMBODIMENTS OF THE INVENTION

The present invention will be described in more detail below.

The oral composition of the present invention for reducing dentinal hypersensitivity contains a phosphorylcholine-containing polymer as an active ingredient. The dentinal hypersensitivity-reducing oral composition of the present invention may contain only the phosphorylcholine-containing polymer, and preferably further contains a water. In the case of using the water, the phosphorylcholine-containing polymer is dissolved or dispersed in the water. It is preferred from the viewpoint of safety that the water is a purified water, a pure water, an ion-exchanged water, or the like.

Preferred examples of the phosphorylcholine-containing polymers include homopolymers of a phosphorylcholine-containing monomer and copolymers of the phosphorylcholine-containing monomer and a (meth)acrylic acid derivative monomer. The phosphorylcholine-containing monomer is preferably 2-methacryloyloxyethyl phosphorylcholine (MPC).

Specific examples of such phosphorylcholine-containing polymers include homopolymers of MPC, copolymers of MPC and methyl acrylate, copolymers of MPC and ethyl (meth)acrylate, copolymers of MPC and butyl (meth)acrylate, copolymers of MPC and lauryl acrylate, copolymers of MPC and stearyl (meth)acrylate, copolymers of MPC and 2-ethylhexyl acrylate, copolymers of MPC and benzyl (meth)acrylate, copolymers of MPC and phenoxyethyl (meth)acrylate, copolymers of MPC and cyclohexyl (meth)acrylate, copolymers of MPC and polypropylene glycol mono(meth)acrylate, copolymers of MPC and polytetramethylene glycol mono(meth)acrylate, copolymers of MPC and polypropylene glycol di(meth)acrylate, copolymers of MPC and polytetramethylene glycol mono(meth)acrylate, copolymers of MPC and polypropylene glycol/polyethylene glycol mono(meth)acrylate, and copolymers of MPC and 2-hydroxy-3-methacryloyloxypropyl trimethyl ammonium chloride. Particularly preferred among them are homopolymers of 2-methacryloyloxyethyl phosphorylcholine, copolymers of 2-methacryloyloxyethyl phosphorylcholine and butyl methacrylate, copolymers of 2-methacryloyloxyethyl phosphorylcholine and stearyl methacrylate, and copolymers of 2-methacryloyloxyethyl phosphorylcholine and 2-hydroxy-3-methacryloyloxypropyl trimethyl ammonium chloride.

More specifically, homopolymers of MPC prepared by a polymerization method according to JP 10-298240 A, copolymers of MPC and butyl methacrylate prepared by a polymerization method according to JP 11-035605 A, copolymers of MPC and butyl methacrylate prepared by a polymerization method according to JP 2004-196868 A, copolymers of MPC and stearyl methacrylate prepared by a polymerization method according to JP 2004-196868 A, and copolymers of MPC and 2-hydroxy-3-methacryloyloxypropyl trimethyl ammonium chloride prepared by a polymerization method according to JP 2004-189678 A can be used as the phosphorylcholine-containing polymer in the present invention.

In a case where the phosphorylcholine-containing polymer is the copolymer of the phosphorylcholine-containing monomer and the (meth)acrylic acid derivative monomer, the copolymerization ratio of the phosphorylcholine-containing monomer is preferably 30% by mole or more. The upper limit of the copolymerization ratio is not particularly restricted. When the copolymerization ratio is within this range, the phosphorylcholine-containing polymer exhibits an excellent dentinal hypersensitivity-reducing action.

The phosphorylcholine-containing polymer, which is used as an active ingredient in the dentinal hypersensitivity-reducing oral composition of the present invention, preferably has a weight-average molecular weight of 10,000 to 10,000,000. The weight-average molecular weight is more preferably 50,000 to 5,000,000 in view of a mixing process in production of the phosphorylcholine-containing polymer. When the weight-average molecular weight is too low, the phosphorylcholine-containing polymer does not exhibit an effect appropriate for the amount of the polymer. When the weight-average molecular weight is too high, the phosphorylcholine-containing polymer exhibits a flavoring effect, but may cause a bad use feeling. For example, a coating of the polymer may have an excessively strong presence in an oral cavity.

The oral composition of the present invention may contain an ingredient other than the above described water. Specifically, the oral composition may be an oral care product such as a dentifrice, a mouthwash, a mouth freshener, or an oral rinse.

The oral composition may be prepared in a form of a liquid, a viscous liquid, a gel, an emulsion, a solid such as a tablet, or the like, without particular restrictions.

In the oral composition of the present invention, the concentration of the phosphorylcholine-containing polymer is preferably 0.001% to 10% by mass. When the concentration is within this range, the oral composition exhibits a good dentinal hypersensitivity-reducing effect. When the concentration is more than 10% by mass, the oral composition has an excessively high viscosity and thus may exhibit a poor handling property in use.

The oral composition of the present invention preferably has a pH of 5 to 11. When the composition is not a solid, the pH is that of the oral composition per se. When the composition is a solid, the pH is that of a solution or dispersion containing 10% by mass of the composition in water.

The oral composition of the present invention may contain another ingredient. Examples of the other ingredients include buffers, wetters, antiphlogistics, hemostats, hypersensitivity-reducing agents, tooth decay-preventing agents, tartar deposition-preventing agents, mouth deodorants, astringents, dental plaque removers, vitamin supplements, washing aids, surfactants, antiseptic disinfectants, sweeteners, thickeners, solvents, colorants, organic acids, inorganic salts, antioxidants, stabilizers, preservatives, sequestrants, fragrances, flavoring agents, fresheners, and dyes.

Examples of the buffers include, but not limited thereto, citric acid, phosphoric acid, malic acid, gluconic acid, and salts thereof. The content of the buffer is preferably 0.01% to 3% by mass based on the entire oral composition in view of controlling the pH of the oral composition at 5 to 11.

Examples of the wetters include polyols such as glycerin, propylene glycol, butylene glycol, pentylene glycol, dipropylene glycol, polyethylene glycol, xylitol, sorbitol, mannitol, maltitol, and erythritol. In a case where the oral composition contains at least one ingredient selected from the group consisting of glycerin, sorbitol, maltitol, and xylitol, the oral composition can exhibit an improved moisturizing effect in the oral cavity without decrease of the dentinal hypersensitivity-reducing effect. The content of the wetter is preferably 1% to 25% by mass based on the entire oral composition.

Examples of the antiphlogistics include, but not limited thereto, sodium azulene sulfonate, allantoin, aluminum chlorohydroxyallantoinate, aluminum hydroxyallantoinate, epidihydroxycholesterol, dihydrocholesterol, glycyrrhizic acid and salts thereof, β-glycyrrhetinic acid, lysozyme chloride, and methyl salicylate.

Examples of the hemostats include, but not limited thereto, epsilon-aminocaproic acid and tranexamic acid.

Examples of the hypersensitivity-reducing agents include, but not limited thereto, potassium nitrate and aluminum lactate.

Examples of the tooth decay-preventing agents include, but not limited thereto, sodium fluoride and sodium monofluorophosphate.

Examples of the tartar deposition-preventing agents include, but not limited thereto, disodium dihydrogen pyrophosphate, sodium pyrophosphate, and zinc chloride.

Examples of the mouth deodorants include, but not limited thereto, sodium copper chlorophyllin.

Examples of the astringents include, but not limited thereto, sodium chloride and 1-menthol.

Examples of the dental plaque removers include, but not limited thereto, polyethylene glycols and polyvinylpyrrolidones.

Examples of the vitamin supplements include, but not limited thereto, ascorbic acid and salts thereof, pyridoxine hydrochloride, dl-α-tocopherol acetate, and dl-α-tocopherol nicotinate.

Examples of the washing aids include, but not limited thereto, zeolites, sodium monohydrogen phosphate, trisodium phosphate, and sodium polyphosphate.

Examples of the surfactants include, but not limited thereto, polyoxyethylene lauryl ethers (8 to 10 E.O.), sodium lauroyl sarcosinate, polyoxyethylene hardened castor oils, polyoxyethylene sorbitan fatty acid esters, polyglycerin fatty acid esters, acylamino acid salts, fatty acid amide propyl betaines, and fatty acid amide betaines. It is particularly preferred that the oral composition contains 0.05% to 2% by mass of a polyoxyethylene hardened castor oil or a polyoxyethylene sorbitan fatty acid ester.

Examples of the antiseptic disinfectants include, but not limited thereto, isopropylmethylphenol, cetylpyridinium chloride, dequalinium chloride, benzalkonium chloride, benzethonium chloride, alkyldiaminoethylglycine hydrochlorides, chlorhexidine hydrochloride, chlorhexidine gluconate, triclosan, 1,8-cineole, polyhexanide hydrochloride, hinokitiol, benzoic acid and salts thereof, and paraben-based substances.

Examples of the sweeteners include, but not limited thereto, saccharin, stevioside, sucrose, aspartame, and licorice extracts.

Examples of the thickeners include, but not limited thereto, cellulose-based thickeners such as methylcelluloses, hydroxyethylcelluloses, hydroxypropylcelluloses, hydroxypropylmethylcelluloses, and carboxymethylcelluloses, and polysaccharides such as hyaluronic acids and salts thereof, chondroitin sulfates and salts thereof, alginic acids and salts thereof, gellan gums, and xanthane gums.

Examples of the solvents include, but not limited thereto, ethanol and the like, in addition to the above-described waters.

The solvent, colorant, organic acid, inorganic salt, antioxidant, stabilizer, preservative, sequestrant, fragrance, flavoring agent, freshener, and dye may be selected from conventional ones for oral compositions.

The method of the present invention for reducing the dentinal hypersensitivity contains bringing the oral composition of the present invention into contact with an oral cavity of a user. For example, the oral composition may be brought into contact with the oral cavity of the user by rinsing the user's mouth with the oral composition, by brushing the user's teeth using the oral composition as the dentifrice, by spraying the oral composition onto the oral cavity, or by gargling with the oral composition.

EXAMPLES

The present invention and the advantageous effects will be described more specifically below with reference to Examples and Comparative Examples without intention of restricting the invention.

1. Evaluation of Improvement of Pain Caused by Dentinal Hypersensitivity

Dentinal hypersensitivity-reducing oral compositions of Examples and compositions of Comparative Examples were each evaluated with respect to prevention or reduction of dentinal hypersensitivity pain immediately after use and 2 hours after use.

Triers for conducting the evaluation were persons who suffered dental hypersensitivity pain every day or 2 to 3 times a week over the last one month.

In the evaluation, each of three triers used the composition, and put cold water (4° C.) in mouth to evaluate the dentinal hypersensitivity pain immediately after and 2 hours after the use. The dentinal hypersensitivity pain was rated on a scale of 1 to 3, with 3 indicating that the trier felt no pain, 2 indicating that the trier felt slight pain, and 1 indicating that the trier felt pain. The average value of the rating values was considered as the dentinal hypersensitivity pain evaluation result of the composition. A larger average value means that the dentinal hypersensitivity pain is prevented or reduced more effectively by the composition.

2. Evaluation of Moisture Retention in Oral Cavity

Dentinal hypersensitivity-reducing oral compositions of Examples and compositions of Comparative Examples were each evaluated with respect to moisture retention in oral cavity before and after use.

Triers for conducting the evaluation were persons who suffered dental hypersensitivity pain every day or 2 to 3 times a week over the last one month.

In the evaluation, each of three triers used the composition, and the moisture retention in the oral cavity was measured before and after the use by the oral moisture checker MUCUS (trademark) available from K. K. Life. In each trier, the moisture retention measured before the use was defined as a reference value of 100, and the moisture retention measured after the use was converted to a value relative to the reference value.

Examples 1-1 to 1-12

Dentinal hypersensitivity-reducing oral compositions shown in Table 1 were prepared in the following manner.

In Examples 1-1 to 1-6 and 1-8 to 1-12, a phosphorylcholine-containing polymer was added to a purified water, stirred at the room temperature for 10 minutes, and thereby dissolved in the purified water to prepare a dentinal hypersensitivity-reducing oral composition in the form of an aqueous solution. The pH of the oral composition was measured.

In Example 1-7, a copolymer of MPC and stearyl methacrylate was added little by little to a purified water at 80° C. and subjected to an ultrasonic treatment to prepare a dispersion. The dispersion was cooled to the room temperature to prepare a dentinal hypersensitivity-reducing oral composition in the form of an aqueous dispersion. The pH of the oral composition was measured.

The dentinal hypersensitivity-reducing oral composition of each Example was used as a mouthwash, and was evaluated with respect to the dentinal hypersensitivity pain improvement and the moisture retention in oral cavity as described above. The results are shown in Table 1.

Comparative Examples 1-1 to 1-4

In Comparative Examples 1-1 to 1-4, a soybean lecithin was added little by little to a purified water at 80° C., and subjected to an ultrasonic treatment to prepare a dispersion. The dispersion was cooled to the room temperature to prepare a composition shown in Table 2. The pH of the composition was measured.

The composition of each Comparative Example was used in the same manner as above-described Examples, and was evaluated with respect to the dentinal hypersensitivity pain improvement and the moisture retention in oral cavity as described above. The results are shown in Table 2.

TABLE 1

| | | Ex. 1-1 | Ex. 1-2 | Ex. 1-3 | Ex. 1-4 | Ex. 1-5 | Ex. 1-6 | Ex. 1-7 | Ex. 1-8 | Ex. 1-9 | Ex. 1-10 | Ex. 1-11 | Ex. 1-12 |
|---|---|---|---|---|---|---|---|---|---|---|---|---|---|
| Ingredient | MPC homopolymer (Mw 100,000) | 1.00 | | | | | | | | 0.50 | 0.25 | | |
| | MPC/butyl methacrylate copolymer 1 (Mw 600,000) | | 0.10 | 1.00 | 5.00 | 10.00 | | | | 0.50 | 0.25 | 0.50 | 0.50 |
| | MPC/butyl methacrylate copolymer 2 (Mw 100,000) | | | | | | 1.00 | | | | | 0.50 | |
| | MPC/stearyl methacrylate copolymer (Mw 250,000) | | | | | | | 0.05 | | | | | |
| | MPC/2-hydroxy-3-methacryloyloxypropyl trimethyl ammonium copolymer (Mw 450,000) | | | | | | | | 1.00 | | 0.50 | | 0.50 |
| | Purified water | 99.00 | 99.90 | 99.00 | 95.00 | 90.00 | 99.00 | 99.95 | 99.00 | 99.00 | 99.00 | 99.00 | 99.00 |
| | Total | 100.00 | 100.00 | 100.00 | 100.00 | 100.00 | 100.00 | 100.00 | 100.00 | 100.00 | 100.00 | 100.00 | 100.00 |
| | pH | 5.0 | 5.0 | 5.0 | 5.0 | 5.0 | 5.0 | 5.0 | 5.0 | 5.0 | 5.0 | 5.0 | 5.0 |
| Evaluation of pain | Immediately after use | 2.4 | 2.2 | 2.4 | 2.5 | 2.8 | 2.4 | 2.2 | 2.4 | 2.6 | 2.4 | 2.5 | 2.6 |
| | 2 hours after use | 2.2 | 2.1 | 2.2 | 2.4 | 2.6 | 2.2 | 2.1 | 2.2 | 2.3 | 2.4 | 2.3 | 2.5 |
| Evaluation of moisture retention in oral cavity | 2 hours after use | 101 | 100 | 101 | 103 | 105 | 101 | 100 | 101 | 101 | 101 | 101 | 101 |

MPC/butyl methacrylate copolymer 1: copolymerization ratio MPC:butyl methacrylate = 8:2 (mole ratio, the same applies to the following)
MPC/butyl methacrylate copolymer 2: copolymerization ratio MPC:butyl methacrylate = 3:7 (mole ratio, the same applies to the following)

TABLE 2

|  |  | Comp. Ex. 1-1 | Comp. Ex. 1-2 | Comp. Ex. 1-3 | Comp. Ex. 1-4 |
|---|---|---|---|---|---|
| Ingredient | Soybean lecithin | 0.10 | 1.00 | 5.00 | 10.00 |
|  | Purified water | 99.90 | 99.00 | 95.00 | 90.00 |
|  | Total | 100.00 | 100.00 | 100.00 | 100.00 |
|  | pH | 5.0 | 5.0 | 5.0 | 5.0 |
| Evaluation of pain | Immediately after use | 1.0 | 1.0 | 1.0 | 1.1 |
|  | 2 hours after use | 1.0 | 1.0 | 1.0 | 1.0 |
| Evaluation of moisture retention in oral cavity | 2 hours after use | 100 | 100 | 99 | 99 |

Examples 2-1 to 2-8

Oral compositions shown in Table 3 were prepared in the following manner.

Ingredients other than phosphorylcholine-containing polymers were added in arbitrary order to a purified water, mixed at the room temperature for 10 minutes, and thereby dissolved in the purified water. After confirmation of the dissolving, a phosphorylcholine-containing polymer was added thereto, mixed at the room temperature for 10 minutes, and thereby dissolved in the solution, to prepare an oral composition. The pH of the oral composition was measured.

The oral composition of each Example was used as a mouthwash, and was evaluated with respect to the dentinal hypersensitivity pain improvement and the moisture retention in oral cavity as described above. The results are shown in Table 3.

Comparative Examples 2-1 to 2-4

In Comparative Examples 2-1 to 2-4, a soybean lecithin was added little by little to a purified water at 80° C., and subjected to an ultrasonic treatment to prepare a dispersion. The dispersion was cooled to the room temperature. Then, sodium hydrogen phosphate and sodium dihydrogen phosphate were added thereto successively, glycerin was further added in Comparative Example 2-4, and the resultant was mixed for 5 minutes, so that the ingredients were dissolved in the purified water, to prepare each composition shown in Table 4. The pH of the composition was measured.

The composition of each Comparative Example was used in the same manner as above-described Examples, and was evaluated with respect to the dentinal hypersensitivity pain improvement and the moisture retention in oral cavity as described above. The results are shown in Table 4.

TABLE 3

|  |  | Ex. 2-1 | Ex. 2-2 | Ex. 2-3 | Ex. 2-4 | Ex. 2-5 | Ex. 2-6 | Ex. 2-7 | Ex. 2-8 |
|---|---|---|---|---|---|---|---|---|---|
| Ingredient | MPC homopolymer (Mw 100,000) | 0.50 |  |  |  |  |  |  |  |
|  | MPC/butyl methacrylate copolymer 1 (Mw 600,000) |  | 0.50 | 0.50 |  |  |  | 0.25 | 0.25 |
|  | MPC/butyl methacrylate copolymer 2 (Mw 100,000) |  |  |  | 0.50 |  |  | 0.25 |  |
|  | MPC/stearyl methacrylate copolymer (Mw 250,000) |  |  |  |  | 0.50 | 0.50 |  | 0.25 |
|  | MPC/2-hydroxy-3-methacryloyloxypropyl trimethyl ammonium copolymer (Mw 450,000) |  |  |  |  |  |  |  |  |
|  | Sodium hydrogen phosphate | 0.20 |  | 0.25 |  | 0.22 | 0.21 |  | 0.21 |
|  | Sodium dihydrogen phosphate | 0.40 |  | 0.40 |  | 0.40 | 0.40 |  | 0.40 |
|  | Citric acid |  | 0.05 |  | 0.05 |  |  | 0.05 |  |
|  | Sodium citrate |  | 0.40 |  | 0.40 |  |  | 0.40 |  |
|  | Glycerin | 3.00 |  | 8.00 |  |  |  |  | 1.00 |
|  | Sorbitol |  |  |  | 8.00 |  |  |  | 1.00 |
|  | Xylitol | 3.00 | 5.00 |  |  | 8.00 |  | 3.00 | 5.00 |
|  | Maltitol |  |  |  |  |  | 8.00 | 3.00 |  |
|  | Purified water | 92.90 | 94.05 | 90.85 | 91.05 | 90.88 | 90.89 | 93.05 | 91.89 |
|  | Total | 100.00 | 100.00 | 100.00 | 100.00 | 100.00 | 100.00 | 100.00 | 100.00 |
|  | pH | 6.5 | 6.5 | 6.5 | 6.5 | 6.5 | 6.5 | 6.5 | 6.5 |
| Evaluation of pain | Immediately after use | 2.6 | 2.6 | 2.6 | 2.6 | 2.6 | 2.6 | 2.6 | 2.6 |
|  | 2 hours after use | 2.4 | 2.4 | 2.4 | 2.5 | 2.5 | 2.4 | 2.5 | 2.4 |
| Evaluation of moisture retention in oral cavity | 2 hours after use | 110 | 110 | 113 | 110 | 109 | 112 | 110 | 110 |

MPC/butyl methacrylate copolymer 1: copolymerization ratio 8:2 (mole ratio)
MPC/butyl methacrylate copolymer 2: copolymerization ratio 3:7 (mole ratio)

TABLE 4

|  |  | Comp. Ex. 2-1 | Comp. Ex. 2-2 | Comp. Ex. 2-3 | Comp. Ex. 2-4 |
|---|---|---|---|---|---|
| Ingredient | Soybean lecithin | 0.10 | 1.00 | 5.00 | 5.00 |
|  | Sodium hydrogen phosphate | 0.20 | 0.20 | 0.20 | 0.20 |

TABLE 4-continued

|  |  | Comp. Ex. 2-1 | Comp. Ex. 2-2 | Comp. Ex. 2-3 | Comp. Ex. 2-4 |
|---|---|---|---|---|---|
|  | Sodium dihydrogen phosphate | 0.40 | 0.40 | 0.40 | 0.40 |
|  | Glycerin |  |  |  | 8.00 |
|  | Purified water | 99.30 | 98.40 | 94.40 | 86.40 |
|  | Total | 100.00 | 100.00 | 100.00 | 100.00 |
|  | pH | 6.5 | 6.5 | 6.5 | 6.5 |
| Evaluation of pain | Immediately after use | 1.0 | 1.0 | 1.0 | 1.1 |
|  | 2 hours after use | 1.0 | 1.0 | 1.0 | 1.0 |
| Evaluation of moisture retention in oral cavity | 2 hours after use | 100 | 99 | 98 | 101 |

Example 3-1

An oral composition shown in Table 5 was prepared as a dentifrice in the following manner.

In a vacuum mixer, ingredients of addition order A were added to a purified water at the room temperature, dispersed for 5 minutes, and heated to 80° C. and dissolved in the purified water. Ingredients of addition order B were added thereto and mixed. After confirmation of dissolution, ingredients of addition order C were added thereto and dissolved therein. The resultant was mixed for 30 minutes, cooled, and degassed under reduced pressure, to prepare an oral composition as a dentifrice. The pH of the oral composition was measured.

The oral composition was used as a dentifrice, and was evaluated with respect to the dentinal hypersensitivity pain improvement and the moisture retention in oral cavity as described above. The results are shown in Table 5.

Examples 3-2 to 3-12

Oral compositions were prepared as dentifrices in the same manner as Example 3-1 except that the types and amounts of the ingredients were changed as shown in Table 5. The pH of each oral composition was measured.

The oral composition of each Example was used as a dentifrice, and was evaluated with respect to the dentinal hypersensitivity pain improvement and the moisture retention in oral cavity as described above. The results are shown in Table 5.

TABLE 5

|  |  | Order | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 | Ex. 3-11 | Ex. 3-12 |
|---|---|---|---|---|---|---|---|---|---|---|---|---|---|---|
| Ingredient | MPC homopolymer (Mw 100,000) | A | 0.10 | 1.00 |  |  |  |  |  |  |  |  |  |  |
|  | MPC/butyl methacrylate copolymer 1 (Mw 600,000) |  |  |  | 0.10 | 1.00 |  |  |  |  |  |  | 0.50 | 0.50 |
|  | MPC/butyl methacrylate copolymer 2 (Mw 100,000) |  |  |  |  |  | 0.10 | 1.00 |  |  |  | 0.50 |  |  |
|  | MPC/stearyl methacrylate copolymer (Mw 250,000) |  |  |  |  |  |  |  | 0.05 | 0.50 |  |  |  |  |
|  | MPC/2-hydroxy-3-methacryloyloxypropyl trimethyl ammonium copolymer (Mw 450,000) |  |  |  |  |  |  |  |  |  | 0.10 | 1.00 |  | 0.50 |
|  | Glycerin |  | 15.00 |  | 12.00 | 12.00 |  |  | 8.00 | 8.00 |  | 12.00 | 12.00 | 12.00 |
|  | Sorbitol |  |  | 15.00 |  |  | 12.00 | 15.00 |  |  | 14.00 |  |  |  |
|  | Xylitol |  |  |  | 5.00 |  | 5.00 |  | 5.00 | 5.00 |  | 3.00 | 3.00 | 3.00 |
|  | Maltitol |  |  |  |  | 5.00 |  |  |  |  |  |  |  |  |
|  | Propylene glycol |  |  |  |  | 2.00 |  |  |  |  |  | 3.00 | 3.00 | 3.00 |
|  | Hydroxyethylcellulose |  | 1.20 | 1.20 | 1.20 | 1.20 | 1.50 | 1.50 | 1.30 | 1.50 | 1.30 | 1.20 | 1.20 | 1.20 |
|  | Silicic anhydride | B | 2.00 | 2.00 | 2.00 | 2.00 | 2.00 | 2.00 | 2.00 | 2.00 | 2.00 | 2.00 | 2.00 | 2.00 |
|  | Calcium phosphate |  | 45.00 | 45.00 | 45.00 | 45.00 | 45.00 | 45.00 | 45.00 | 45.00 | 45.00 | 45.00 | 45.00 | 45.00 |
|  | Sodium lauryl sulfate |  | 1.50 | 1.50 | 1.50 | 1.50 | 1.50 | 1.50 | 1.50 | 1.50 | 1.50 | 1.50 | 1.50 | 1.50 |
|  | DL-Malic acid | C |  | 0.20 |  |  |  |  |  |  |  |  |  |  |
|  | Citric acid |  |  |  |  |  | 0.20 |  |  |  | 0.05 |  |  |  |
|  | Sodium fluoride |  | 0.19 | 0.19 | 0.19 | 0.19 | 0.19 | 0.19 | 0.19 | 0.19 | 0.19 | 0.19 | 0.19 | 0.19 |
|  | Isopropylmethylphenol |  | 0.05 |  |  |  | 0.05 |  |  | 0.05 |  | 0.05 | 0.05 | 0.05 |
|  | Cetylpyridinium chloride |  |  | 0.05 |  |  |  |  | 0.05 |  | 0.05 |  |  |  |

TABLE 5-continued

|  | Order | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 | Ex. 3-11 | Ex. 3-12 |
|---|---|---|---|---|---|---|---|---|---|---|---|---|---|
| Benzethonium chloride | | | | | 0.01 | 0.01 | | 0.01 | | | | | |
| Dipotassium glycyrrhizinate | | 0.20 | | 0.20 | | | 0.20 | | | 0.20 | 0.20 | 0.20 | 0.20 |
| Ethyl p-hydroxybenzoate | | 0.01 | 0.01 | 0.01 | 0.01 | 0.01 | 0.01 | 0.01 | 0.01 | 0.01 | 0.01 | 0.01 | 0.01 |
| Purified water | A | 34.75 | 33.85 | 32.79 | 30.09 | 32.45 | 33.59 | 36.90 | 36.25 | 35.60 | 30.85 | 30.85 | 30.85 |
| Total | | 100.00 | 100.00 | 100.00 | 100.00 | 100.00 | 100.00 | 100.00 | 100.00 | 100.00 | 100.00 | 100.00 | 100.00 |
| pH | | 10.0 | 10.0 | 10.0 | 10.0 | 10.0 | 10.0 | 10.0 | 10.0 | 10.0 | 10.0 | 10.0 | 10.0 |
| Evaluation of pain — Immediately after use | | 2.2 | 2.4 | 2.2 | 2.4 | 2.3 | 2.5 | 2.3 | 2.4 | 2.2 | 2.4 | 2.4 | 2.4 |
| Evaluation of pain — 2 hours after use | | 2.1 | 2.2 | 2.1 | 2.2 | 2.2 | 2.3 | 2.2 | 2.4 | 2.1 | 2.3 | 2.3 | 2.3 |
| Evaluation of moisture retention in oral cavity — 2 hours after use | | 106 | 108 | 106 | 107 | 106 | 107 | 104 | 106 | 104 | 105 | 107 | 106 |

MPC/butyl methacrylate copolymer 1: copolymerization ratio 8:2 (mole ratio)
MPC/butyl methacrylate copolymer 2: copolymerization ratio 3:7 (mole ratio)

Examples 4-1 to 4-7

Oral compositions shown in Table 6 were prepared as mouthwashes in the following manner.

A purified water was heated to 80° C., and ingredients shown in Table 6 were dissolved in the purified water in amounts shown in Table 6, to prepare an oral composition as a mouthwash. Incidentally, in the case of using a lemon oil as a fragrance, the lemon oil was preliminarily mixed with a polyoxy hardened castor oil or a polysorbate 80, and then added to the purified water at 80° C. The pH of each mouthwash of the oral composition was measured.

The oral composition of each Example was used as a mouthwash, and was evaluated with respect to the dentinal hypersensitivity pain improvement and the moisture retention in oral cavity as described above. The results are shown in Table 6.

TABLE 6

| | | Ex. 4-1 | Ex. 4-2 | Ex. 4-3 | Ex. 4-4 | Ex. 4-5 | Ex. 4-6 | Ex. 4-7 |
|---|---|---|---|---|---|---|---|---|
| Ingredient | MPC homopolymer (Mw 100,000) | 0.50 | | | | | | |
| | MPC/butyl methacrylate copolymer 1 (Mw 600,000) | | 0.50 | | | | 0.50 | 0.50 |
| | MPC/butyl methacrylate copolymer 2 (Mw 100,000) | | | 0.50 | | | 0.50 | |
| | MPC/stearyl methacrylate copolymer (Mw 250,000) | | | | 0.05 | | | |
| | MPC/2-hydroxy-3-methacryloyloxypropyl trimethyl ammonium copolymer (Mw 450,000) | | | | | 1.00 | | 0.50 |
| | Sodium dihydrogen phosphate | 0.10 | 0.10 | | | | | |
| | Sodium citrate | | | 0.20 | 0.20 | 0.20 | 0.20 | 0.20 |
| | Glycerin | 10.00 | 8.00 | | | | | |
| | Sorbitol | | | 15.00 | 15.00 | 15.00 | 10.00 | 8.00 |
| | Xylitol | 5.00 | | 3.00 | | | | |
| | Maltitol | | 2.00 | | 3.00 | 3.00 | 3.00 | 3.00 |
| | Cetylpyridinium chloride | | | 0.05 | 0.05 | 0.01 | | |
| | Benzethonium chloride | 0.01 | 0.01 | | | | 0.01 | 0.01 |
| | Polyoxyethylene hardened castor oil | | 2.00 | | | | | |
| | Polysorbate 80 | | | 1.00 | | 0.50 | 0.50 | 0.50 |
| | Dipotassium glycyrrhizinate | | | 0.05 | 0.10 | 0.10 | | |
| | Fragrance (lemon oil) | | 0.05 | 0.05 | | | | |
| | Ethyl p-hydroxybenzoate | 0.01 | 0.01 | 0.01 | 0.01 | 0.01 | 0.01 | 0.01 |
| | Ethanol | 15.00 | | 15.00 | | | | |
| | Purified water | 69.38 | 87.33 | 65.14 | 81.59 | 80.18 | 85.28 | 87.28 |
| | Total | 100.00 | 100.00 | 100.00 | 100.00 | 100.00 | 100.00 | 100.00 |
| | pH | 6.8 | 6.8 | 6.8 | 6.8 | 6.8 | 6.8 | 6.8 |
| Evaluation of pain | Immediately after use | 2.7 | 2.7 | 2.7 | 2.4 | 2.5 | 2.5 | 2.5 |
| | 2 hours after use | 2.4 | 2.4 | 2.5 | 2.2 | 2.3 | 2.3 | 2.3 |

TABLE 6-continued

|  |  | Ex. 4-1 | Ex. 4-2 | Ex. 4-3 | Ex. 4-4 | Ex. 4-5 | Ex. 4-6 | Ex. 4-7 |
|---|---|---|---|---|---|---|---|---|
| Evaluation of moisture retention in oral cavity | 2 hours after use | 106 | 112 | 112 | 105 | 111 | 111 | 109 |

MPC/butyl methacrylate copolymer 1: copolymerization ratio 8:2 (mole ratio)
MPC/butyl methacrylate copolymer 2: copolymerization ratio 3:7 (mole ratio)

Examples 5-1 to 5-5

Oral compositions shown in Table 7 were prepared as mouth fresheners in the following manner.

Ingredients of addition order B were dissolved in ethanol at the room temperature to prepare an ethanol solution. Separately, ingredients of addition order A were dissolved in a purified water at the room temperature to prepare an aqueous solution. The aqueous solution was added to the ethanol solution, and mixed and dissolved for 10 minutes to prepare each oral composition as a mouth freshener. The pH of each oral composition was measured.

The oral composition of each Example was sprayed as a mouth freshener onto an oral cavity, and was evaluated with respect to the dentinal hypersensitivity pain improvement and the moisture retention in oral cavity as described above. The results are shown in Table 7.

Examples 6-1 to 6-5

Oral compositions shown in Table 8 were prepared as oral rinses in the following manner.

Ingredients of addition order A were dissolved in a purified water at the room temperature to prepare an aqueous solution. Separately, ingredients of addition order B were dissolved in ethanol at the room temperature to prepare an ethanol solution. The ethanol solution was added to the aqueous solution, and mixed and dissolved for 10 minutes to prepare each oral composition as an oral rinse. The pH of each oral composition was measured.

The oral composition of each Example was used as an oral rinse, and was evaluated with respect to the dentinal hypersensitivity pain improvement and the moisture retention in oral cavity as described above. Incidentally, each oral com-

TABLE 7

|  |  | Order | Ex. 5-1 | Ex. 5-2 | Ex. 5-3 | Ex. 5-4 | Ex. 5-5 |
|---|---|---|---|---|---|---|---|
| Ingredient | MPC homopolymer (Mw 100,000) | A | 1.00 |  |  |  |  |
|  | MPC/butyl methacrylate copolymer 1 (Mw 600,000) |  |  | 1.00 |  |  |  |
|  | MPC/butyl methacrylate copolymer 2 (Mw 100,000) |  |  |  | 1.00 |  |  |
|  | MPC/stearyl methacrylate copolymer (Mw 250,000) |  |  |  |  | 1.00 |  |
|  | MPC/2-hydroxy-3-methacryloyloxypropyl trimethyl ammonium copolymer (Mw 450,000) |  |  |  |  |  | 1.00 |
|  | Glycerin |  | 10.00 | 10.00 |  |  |  |
|  | Sorbitol |  |  |  | 12.00 | 12.00 | 12.00 |
|  | Xylitol |  | 5.00 |  | 5.00 |  |  |
|  | Maltitol |  |  | 5.00 |  | 3.00 | 3.00 |
|  | l-Menthol | B | 0.50 | 0.50 | 0.50 | 0.50 | 0.50 |
|  | Polyoxyethylene hardened castor oil |  | 0.50 | 1.00 | 1.00 | 1.00 |  |
|  | Lemon oil |  | 0.01 | 0.05 | 0.05 |  |  |
|  | Ethanol |  | 40.00 | 40.00 | 40.00 | 40.00 | 40.00 |
|  | Purified water | A | 42.99 | 42.45 | 40.45 | 42.50 | 43.50 |
| Total |  |  | 100.00 | 100.00 | 100.00 | 100.00 | 100.00 |
| pH |  |  | 5.1 | 5.2 | 5.1 | 5.1 | 5.1 |
| Evaluation of pain | Immediately after use |  | 2.8 | 2.8 | 2.8 | 2.8 | 2.5 |
|  | 2 hours after use |  | 2.3 | 2.4 | 2.4 | 2.5 | 2.2 |
| Evaluation of moisture retention in oral cavity | 2 hours after use |  | 108 | 111 | 109 | 110 | 105 |

MPC/butyl methacrylate copolymer 1: copolymerization ratio 8:2 (mole ratio)
MPC/butyl methacrylate copolymer 2: copolymerization ratio 3:7 (mole ratio)

position shown in Table 8 was 50-fold diluted in the use of the oral rinse. The results are shown in Table 8.

weight of 450,000, prepared by a polymerization method described in Examples of JP 2004-189678 A.

TABLE 8

|  |  | Order | Ex. 6-1 | Ex. 6-2 | Ex. 6-3 | Ex. 6-4 | Ex. 6-5 |
|---|---|---|---|---|---|---|---|
| Ingredient | MPC homopolymer (Mw 100,000) | A | 1.00 | | | | |
| | MPC/butyl methacrylate copolymer 1 (Mw 600,000) | | | 1.00 | | | |
| | MPC/butyl methacrylate copolymer 2 (Mw 100,000) | | | | 1.00 | | |
| | MPC/stearyl methacrylate copolymer (Mw 250,000) | | | | | 0.30 | |
| | MPC/2-hydroxy-3-methacryloyloxypropyl trimethyl ammonium copolymer (Mw 450,000) | | | | | | 1.00 |
| | Sodium citrate | | 0.10 | 0.10 | 0.10 | 0.10 | 0.10 |
| | Glycerin | | 15.00 | 8.00 | | | |
| | Sorbitol | | | | 15.00 | 15.00 | 15.00 |
| | Xylitol | | 5.00 | 1.00 | 3.00 | | |
| | Maltitol | | | 1.00 | | 3.00 | 3.00 |
| | Povidone iodine | | 6.80 | | | 6.80 | 6.80 |
| | Cetylpyridinium chloride | | | 0.25 | 0.25 | | |
| | Dipotassium glycyrrhizinate | | | 0.25 | | | |
| | l-Menthol | B | 0.75 | 0.75 | 0.75 | 0.25 | |
| | Polyoxy hardened castor oil | | 1.00 | 1.00 | | 1.00 | |
| | Saccharine sodium | | 0.60 | 0.60 | 0.60 | 0.60 | 0.60 |
| | Ethanol | | 30.00 | 30.00 | 30.00 | 27.95 | 27.95 |
| | Purified water | A | 39.75 | 56.05 | 49.30 | 45.00 | 45.55 |
| Total | | | 100.00 | 100.00 | 100.00 | 100.00 | 100.00 |
| pH | | | 6.8 | 6.8 | 6.8 | 6.8 | 6.8 |
| Evaluation of pain | Immediately after use | | 2.7 | 2.7 | 2.6 | 2.5 | 2.6 |
| | 2 hours after use | | 2.7 | 2.6 | 2.4 | 2.3 | 2.4 |
| Evaluation of moisture retention in oral cavity | 2 hours after use | | 112 | 110 | 106 | 110 | 105 |

MPC/butyl methacrylate copolymer 1: copolymerization ratio 8:2 (mole ratio)
MPC/butyl methacrylate copolymer 2: copolymerization ratio 3:7 (mole ratio)

The polymers shown in the tables will be described in more detail below.

MPC homopolymer: A homopolymer of 2-methacryloyloxyethyl phosphorylcholine, having a weight-average molecular weight of 100,000, prepared by a polymerization method described in Examples of JP 10-298240 A.

MPC/butyl methacrylate copolymer 1: A copolymer of 2-methacryloyloxyethyl phosphorylcholine and butyl methacrylate, having a copolymerization ratio (by mole) of 80/20 and a weight-average molecular weight of 600,000, prepared by a polymerization method described in Examples of JP 11-035605 A.

MPC/butyl methacrylate copolymer 2: A copolymer of 2-methacryloyloxyethyl phosphorylcholine and butyl methacrylate, having a copolymerization ratio (by mole) of 30/70 and a weight-average molecular weight of 100,000, prepared by a polymerization method described in Examples of JP 2004-196868 A.

MPC/stearyl methacrylate copolymer: A copolymer of 2-methacryloyloxyethyl phosphorylcholine and stearyl methacrylate, having a copolymerization ratio (by mole) of 33/67 and a weight-average molecular weight of 250,000, prepared by a polymerization method described in Examples of JP 2004-196868 A.

MPC/2-hydroxy-3-methacryloyloxypropyl trimethyl ammonium copolymer: A copolymer of 2-methacryloyloxyethyl phosphorylcholine and 2-hydroxy-3-methacryloyloxypropyl trimethyl ammonium, having a copolymerization ratio (by mole) of 70/30 and a weight-average molecular With regard to the evaluation of the dentinal hypersensitivity pain improvement, the average values rated by the triers were 2 or more in Examples 1-1 to 1-12, whereas the average values were 1 in Comparative Examples 1-1 to 1-4. Thus, in Examples 1-1 to 1-12, the dentinal hypersensitivity was significantly reduced. It is clear from the results that the phosphorylcholine-containing polymer is useful as an active ingredient for reducing the dentinal hypersensitivity.

Furthermore, the average values rated by the triers were 2 or more in Examples 2-1 to 2-8, whereas the average values were 1 in Comparative Examples 2-1 to 2-4. Thus, also in Examples 2-1 to 2-8, the dentinal hypersensitivity was significantly reduced.

With regard to the evaluation of the moisture retention in oral cavity, the values measured after the use remained approximately the same as the values measured before the use in Comparative Examples 2-1 to 2-4. In contrast, in Examples 2-1 to 2-8, the moisture retentions in oral cavity were higher after the use than before the use, so that the oral compositions exhibited excellent moisturizing effects.

3. Evaluation of Protection of Dentinal Tubule in bovine tooth

Example 7-1

The MPC/butyl methacrylate copolymer 1 (Mw 600,000) was dissolved in a purified water to prepare a dentinal hypersensitivity-reducing oral composition having a concentration of 5% by mass. The oral composition was brought into contact with a bovine tooth with exposed dentinal tubules, and the degree of protection for the dentinal tubules was observed by an electronic microscope.

Specifically, the test was carried out in the following manner. A bovine tooth was taken and cut vertically to the tooth axis using the precision cutter ISOMET (available from Buehler ITW Japan) to prepare bovine tooth sections having a thickness of 1.5 mm. Then, a step of keeping the bovine tooth section in contact with a 50% aqueous citric acid solution for 3 minutes was repeated twice to remove the smear layer. The bovine tooth section was washed with a purified water, and the dentin surface of the section was dried by air blow. The prepared dentinal hypersensitivity-reducing oral composition was left in contact with the bovine tooth section for 30 seconds. Furthermore, the bovine tooth section was left in contact with a 2.5% aqueous glutaraldehyde phosphate buffer for 30 minutes. Finally, the bovine tooth section was sufficiently dried and observed using a scanning electron microscope SU1510 (available from Hitachi High-Technologies Corporation).

Figure 1:
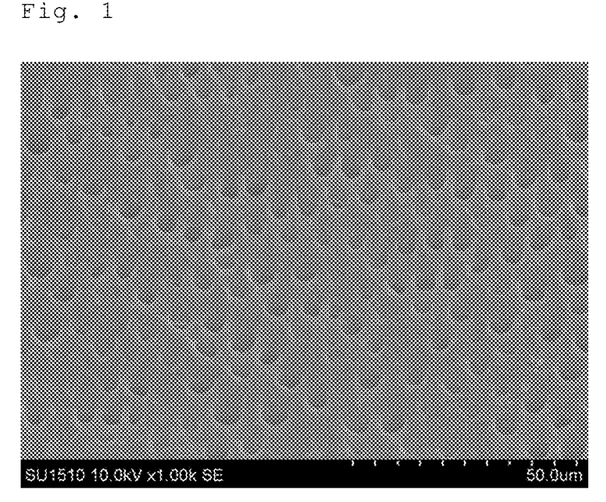
FIG. 1 is an electron micrograph of a dentin surface of a bovine tooth section with a dentinal tubule exposed therefrom.
Figure 2:
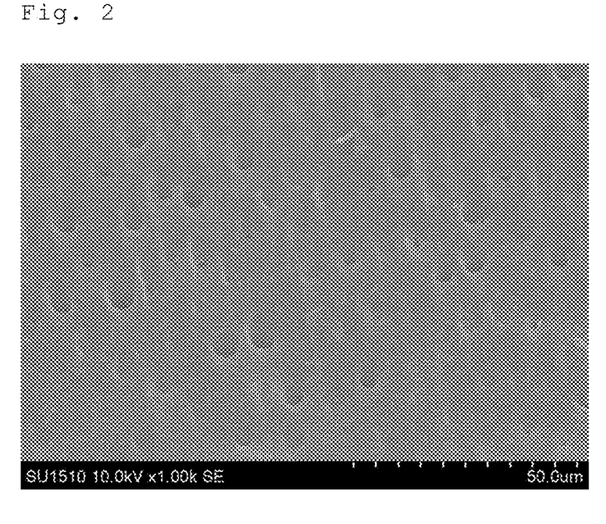
FIG. 2 is an electron micrograph of the dentin surface of the bovine tooth section taken after a dentinal hypersensitivity-reducing oral composition of Example 7-1 is brought into contact with the surface.

An electron micrograph of the untreated bovine tooth with the exposed dentinal tubules is shown in FIG. 1, and an electron micrograph of the bovine tooth taken after the contact with the dentinal hypersensitivity-reducing oral composition is shown in FIG. 2.

Comparative Example 7-1

An aqueous solution containing a polyethylene glycol (PEG, Mw 100,000) at a concentration of 5% by mass was used instead of the dentinal hypersensitivity-reducing oral composition of Example 7-1. This aqueous PEG solution was brought into contact with the bovine tooth having the exposed dentinal tubules in the same manner as Example 7-1.

Figure 3:
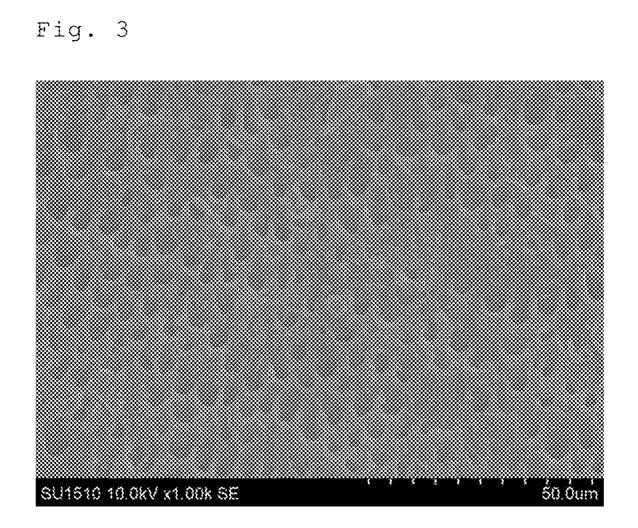
FIG. 3 is an electron micrograph of the dentin surface of the bovine tooth section taken after an aqueous PEG solution of Comparative Example 7-1 is brought into contact with the surface.

An electron micrograph of the bovine tooth taken after the contact with the aqueous PEG solution is shown in FIG. 3.

As is clear from FIGS. 1 to 3, the dentinal hypersensitivity-reducing oral composition of Example 7-1 acted to protect the dentinal tubules significantly, whereas the PEG of Comparative Example 7-1 exhibited no effect of protecting the dentinal tubules.

What is claimed is:

1. A method for reducing dentinal hypersensitivity of a subject suffering from dentinal hypersensitivity, comprising bringing an oral composition comprising a phosphorylcholine-containing polymer as an active ingredient into contact with an oral cavity of the subject.

2. The method according to claim 1, wherein the phosphorylcholine-containing polymer comprises at least one polymer selected from the group consisting of homopolymers of 2-methacryloyloxyethyl phosphorylcholine, copolymers of 2-methacryloyloxyethyl phosphorylcholine and butyl methacrylate, copolymers of 2-methacryloyloxyethyl phosphorylcholine and stearyl methacrylate, and copolymers of 2-methacryloyloxyethyl phosphorylcholine and 2-hydroxy-3-methacryloyloxypropyl trimethyl ammonium chloride, and has a weight-average molecular weight of 10,000 to 10,000,000.

3. The method according to claim 1, wherein the oral composition comprises 0.001% to 10% by mass of the phosphorylcholine-containing polymer.

4. The method according to claim 2, wherein the oral composition comprises 0.001% to 10% by mass of the phosphorylcholine-containing polymer.

5. The method according to claim 1, wherein the oral composition has a pH of 5 to 11.

6. The method according to claim 2, wherein the oral composition has a pH of 5 to 11.

7. The method according to claim 3, wherein the oral composition has a pH of 5 to 11.

8. The method according to claim 1, wherein the oral composition further comprises at least one ingredient selected from the group consisting of glycerin, sorbitol, maltitol, and xylitol.

9. The method according to claim 2, wherein the oral composition further comprises at least one ingredient selected from the group consisting of glycerin, sorbitol, maltitol, and xylitol.

10. The method according to claim 3, wherein the oral composition further comprises at least one ingredient selected from the group consisting of glycerin, sorbitol, maltitol, and xylitol.

11. The method according to claim 4, wherein the oral composition further comprises at least one ingredient selected from the group consisting of glycerin, sorbitol, maltitol, and xylitol.

12. The method according to claim 5, wherein the oral composition further comprises at least one ingredient selected from the group consisting of glycerin, sorbitol, maltitol, and xylitol.

13. The method according to claim 6, wherein the oral composition further comprises at least one ingredient selected from the group consisting of glycerin, sorbitol, maltitol, and xylitol.

14. The method according to claim 7, wherein the oral composition further comprises at least one ingredient selected from the group consisting of glycerin, sorbitol, maltitol, and xylitol.

* * * * *